United States Patent [19]

Ari et al.

[11] Patent Number: 4,684,363
[45] Date of Patent: Aug. 4, 1987

[54] RAPIDLY INFLATABLE BALLOON CATHETER AND METHOD

[75] Inventors: Suha V. Ari, Irvine; Glen L. Lieber, Anaheim, both of Calif.

[73] Assignee: American Hospital Supply Corporation, Evanston, Ill.

[21] Appl. No.: 874,804

[22] Filed: Jun. 13, 1986

Related U.S. Application Data

[63] Continuation of Ser. No. 666,873, Oct. 31, 1984, abandoned.

[51] Int. Cl.$^4$ ............................................ A61M 29/00
[52] U.S. Cl. ...................................... 604/98; 604/104; 128/344
[58] Field of Search ..................... 128/349, 344, 343; 604/96, 97, 98, 99, 102, 104, 52, 53

[56] References Cited

U.S. PATENT DOCUMENTS

| | | | |
|---|---|---|---|
| 2,677,375 | 5/1954 | Raiche | 604/96 |
| 2,936,761 | 5/1960 | Snyder | 128/349 |
| 3,211,150 | 10/1965 | Foderick . | |
| 3,378,011 | 4/1968 | Vitello | 604/98 |
| 3,799,173 | 3/1974 | Kamen | 604/96 |
| 3,825,013 | 7/1974 | Craven . | |
| 3,985,139 | 10/1976 | Penar | 604/99 |
| 3,989,571 | 11/1976 | Harautuncian . | |
| 4,195,637 | 4/1980 | Gleichner et al. . | |
| 4,198,983 | 4/1980 | Becker et al. | 604/96 |
| 4,233,983 | 11/1980 | Rocco . | |
| 4,323,071 | 4/1982 | Simpson et al. . | |
| 4,332,254 | 6/1982 | Lundquist | 604/99 |
| 4,351,342 | 9/1982 | Wiita et al. | 604/97 |
| 4,406,656 | 9/1983 | Hattler et al. . | |
| 4,413,989 | 11/1983 | Schjeldahl et al. . | |
| 4,467,790 | 8/1984 | Schiff | 604/96 |

FOREIGN PATENT DOCUMENTS

| | | |
|---|---|---|
| 0054357 | 6/1982 | European Pat. Off. . |
| 83/03204 | 9/1983 | PCT Int'l Appl. . |
| 84/02069 | 6/1984 | PCT Int'l Appl. . |
| 933375 | 8/1963 | United Kingdom ................ 604/96 |
| 1045202 | 2/1964 | United Kingdom . |
| 1553915 | 6/1976 | United Kingdom . |
| 459237 | 4/1975 | U.S.S.R. ............................. 604/53 |

OTHER PUBLICATIONS

Product Information Sheet of Advanced Cardiovascular Systems for "Simpson-Robert Coronary Balloon Dilatation Catheter", pp. 1-11.

Primary Examiner—Gene Mancene
Assistant Examiner—John G. Weiss
Attorney, Agent, or Firm—Gordon L. Peterson

[57] ABSTRACT

A catheter having first and second lumens and a balloon adjacent the distal end of the catheter, with the first and second lumens extending to the interior of the balloon. Air can be purged from the catheter by introducing a purging liquid in series through the first lumen, the balloon and the second lumen. Following purging, an inflation liquid is introduced in parallel through the first and second lumens to rapidly inflate the balloon. The balloon is rapidly deflated by discharging the inflation liquid from the balloon in parallel through the first and second lumens.

16 Claims, 8 Drawing Figures

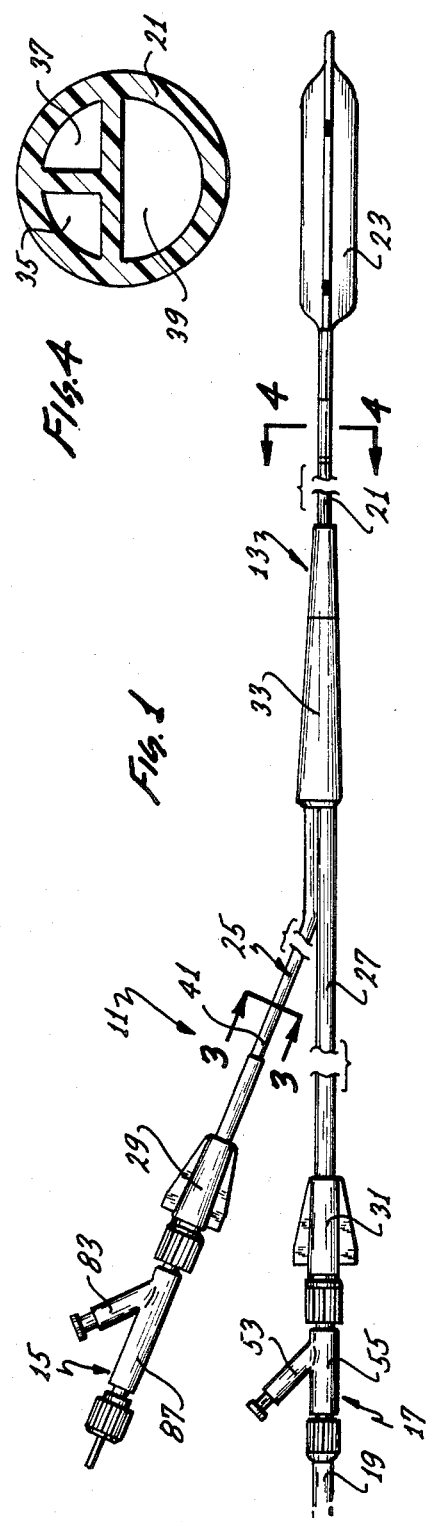
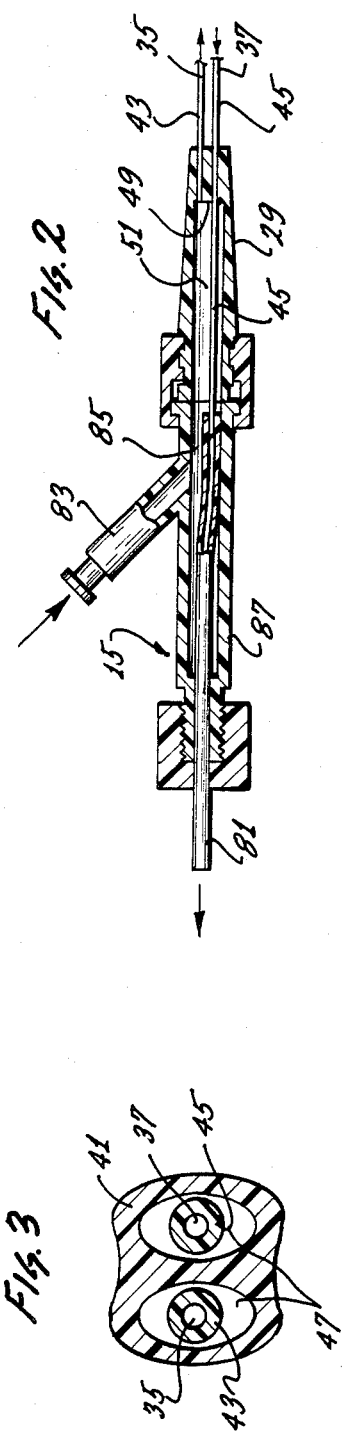

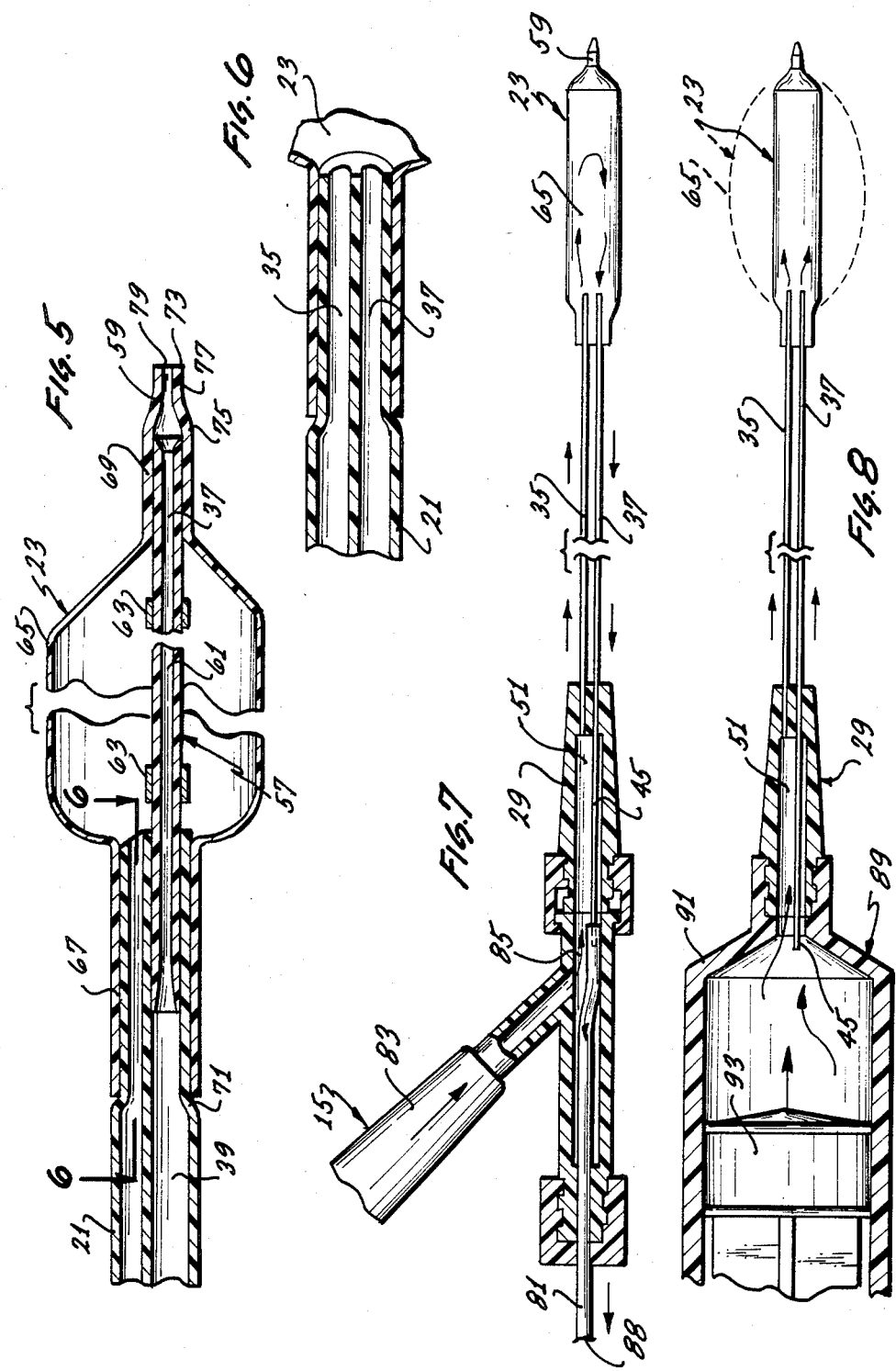

RAPIDLY INFLATABLE BALLOON CATHETER AND METHOD

This application is a continuation of application Ser. No. 666,873 filed Oct. 31, 1984 now abandoned, entitled RAPIDLY INFLATABLE BALLOON CATHETER AND METHOD.

BACKGROUND OF THE INVENTION

In percutaneous transluminal angioplasty, a dilation catheter is inserted into an artery to dilate the artery. For this purpose, the typical dilation catheter has an inflatable balloon adjacent its distal end and a balloon inflation lumen through which the balloon is inflated and deflated. Inflation is accomplished by forcing an appropriate inflation liquid through the lumen to the balloon, and deflation is accomplished by withdrawing the liquid from the balloon. Inflation of the balloon dilates the adjacent regions of the artery to provide lower restriction to blood flow through the artery.

In carrying out the dilation procedure, it is necessary to repeatedly inflate and deflate the balloon to repeatedly dilate the artery. During the time that the balloon is inflated, blood flow through the artery is blocked. For this reason, it is necessary that the inflation and deflation of the balloon be carried out as rapidly as possible. This is difficult to do because the balloon inflation lumen is long and of small diameter, and consequently, the balloon inflation lumen presents a substantial resistance to the flow of the inflation liquid to and from the balloon.

One other complicating factor is that air must be purged from the balloon before the dilation catheter is used for its intended purpose. This can be accomplished, for example, by inserting a vent tube through the balloon inflation lumen into the balloon. A purging liquid is then introduced through the balloon inflation lumen, and the air within the balloon is vented through the vent tube. One example of such an arrangement is shown in Simpson et al U.S. Pat. No. 4,323,071. One problem with this procedure is that the insertion of the vent tube must be carefully carried out not to damage the ballon and may be cumbersome if the vent tube is attempted to be taken out to obtain a larger inflation lumen.

SUMMARY OF THE INVENTION

This invention provides a dilation catheter and method which eliminate the need for vent tube insertion. In addition, with this invention, the balloon of the dilation catheter can be rapidly inflated and deflated so that useful dilation pressure can be applied for the maximum length of time.

This invention provides a catheter assembly adapted to dilate a tubular body member, such as an artery, which comprises a catheter having distal and proximal ends, means for defining at least first and second lumens, and a balloon adjacent the distal end with the first and second lumens extending to the interior of the balloon. The catheter assembly preferably also includes a through lumen that may be used, for example, for a guide wire, monitoring of pressure distally of the balloon, and the infusion of a contrast medium or medication.

To purge air from the balloon, the first and second lumens are used in series. More specifically, a purging liquid is passed in series through the first lumen, the balloon and the second lumen to purge air from the balloon out through the second lumen. Thus, no insertable vent tube is required.

Thereafter, the first and second lumens are used in parallel for inflating and/or deflating of the balloon. Preferably, the first and second lumens are used in parallel for both inflation and deflation of the balloon. This is accomplished by passing an inflation liquid through both of the first and second lumens to inflate the balloon and discharging the inflation liquid from the balloon through both of the first and second lumens.

The purging of air from the balloon is preferably carried out with the balloon pointed downwardly. Following the purging cycle, the catheter can be inserted into the vascular system of the patient to dilate a region of the vascular system.

The catheter assembly includes means for introducing the purging liquid, means for introducing the inflation liquid and means for discharging the inflation liquid from the balloon. Although these means can be of various different constructions, the catheter preferably includes a connector located proximally of the balloon, and the means for introducing the purging liquid is removably coupled to the connector. This permits such means to be removed from the connector and replaced with the means for introducing the inflation liquid.

In a preferred construction, the means for introducing the purging liquid includes a purge fitting having a first leg communicating with the first lumen at the connector and a second leg receiving the second lumen. The first leg is communicable with a source of the purging liquid. The purge fitting can be removed and replaced with, for example, a syringe which can introduce the inflation liquid and enable discharge of the inflation liquid from the balloon.

Another feature of this invention is that the distal tip of the catheter through which the through lumen extends is flexible, of small cross-sectional area and devoid of sharp shoulders. This facilitates insertion and movement of the catheter into and through the vascular system and minimizes the likelihood of damage to the tissue. This feature can be used with advantage with or without the balloon purging and inflation and deflation features of this invention.

This feature can be embodied, for example, in a catheter which includes a catheter body and an extension tube coupled to the catheter body in communication with the through lumen in the catheter body and having a passage therethrough which forms an extension of the through lumen. The balloon has an inflatable portion in communication with a balloon inflation lumen, attachment portions on opposite sides of the inflatable portion sealed to the catheter body and the tube, respectively, and an at least somewhat flexible tubular distal portion extending distally beyond the tube to form an extension of the through lumen and to define a distal end of the catheter. The tubular distal portion is preferably of smaller cross-sectional area than the tube and is smoothly blended into such smaller cross-sectional area to avoid the presence of any sharp or abrupt corners shoulders. Preferably, the tubular distal portion is more flexible than regions of the catheter body adjacent the tube.

The invention, together with additional features and advantages thereof, may best be understood by reference to the following description taken in connection with the accompanying illustrative drawing.

BRIEF DESCRIPTION OF THE DRAWING

FIG. 1 is an elevational view of a catheter assembly constructed in accordance with the teachings of this invention.

FIG. 2 is a partially schematic, longitudinal sectional view through the purge fitting and the associated connector.

FIGS. 3 and 4 are enlarged sectional views taken generally along lines 3—3 and 4—4 of FIG. 1, respectively.

FIG. 5 is an enlarged, fragmentary sectional view taken on an axial plane and showing the distal end portion of the catheter.

FIG. 6 is fragmentary sectional view taken generally along line 6—6 of FIG. 5.

FIGS. 7 and 8 are somewhat schematic views partially in section illustrating the purging and inflation cycles, respectively. The proximal through lumen extension is not shown in FIGS. 7 and 8.

DESCRIPTION OF THE PREFERRED EMBODIMENT

FIG. 1 shows a catheter assembly 11 which includes a catheter 13, a purge fitting 15 and a Y-fitting 17, both of which are coupled to the catheter. The catheter assembly also includes a conventional guidewire introducer 19 partially within the proximal end of the Y-fitting 17.

The catheter 13 includes a catheter body 21, a balloon 23, a vent-inflation extension 25, a through lumen extension 27 and connectors 29 and 31 which define the proximal end of the catheter 13 coupled to the proximal ends of the extensions 25 and 27, respectively. The catheter 13 also includes a sleeve 33 for encasing portions of the extensions 25 and 27 and the catheter body 21.

The catheter body 21 may be in the form of an elongated, flexible, cylindrical tube (FIG. 4) of a suitable plastic material having suitable internal partitions defining portions of balloon lumens 35 and 37 and a through lumen 39. The balloon lumens 35 and 37 extend from the proximal end of the catheter body 21 to the interior of the balloon 23 at the distal end of the catheter body 21 as shown in FIGS. 5 and 6. The balloon lumens 35 and 37 are extended proximally of the catheter body 21 by the extension 25 which comprises an outer tube 41 (FIG. 3) and inner tubes 43 and 45 extending through parallel passages 47 of the outer tube. The outer tube 41 extends within the sleeve 33, and the inner tubes 43 and 45 are received within the lumens 35 and 37 of the catheter body 21 and suitably retained therein. Similarly, the connector 29 is suitably mounted on the outer tube 41. As shown in FIG. 2, the inner tube 43 terminates at an inner face 49 of the connector 29, and the inner tube 45 extends completely through a passage 51 in the connector and completely through the connector.

The through lumen 39 is extended proximally by the extension 27 which extends into the sleeve 33 and a proximal portion of the through lumen 39 in the catheter body 21. The sleeve 33 surrounds the extensions 25 and 27 and the catheter body 21 in a known manner. The Y-fitting 17, which is releasably coupled to the connector 31, has a leg 53 which is open to the through lumen 39 to permit the obtaining of blood pressure or blood samples, the infusion of medication, etc. The Y-fitting 17 has a second leg 55 in which the guidewire introducer 19 is mounted to permit insertion of a guidewire (not shown) through the through lumen 39.

The through lumen 39 is extended distally by a tube 57 and a tubular distal portion 59 of the balloon 23 as shown by way of example in FIG. 5. Although various constructions are possible, the tube 57 is received within a distal end portion of the lumen 39 of the catheter body 21 and is retained therein in any suitable manner, such as by an adhesive or heat sealing. The tube 57 is elongated and flexible and may be constructed of a suitable plastic material. The tube 57 has an axial passage 61 extending through it which forms an extension of the through lumen 39. Preferably, radiopaque bands 63 are suitably retained on the tube 57 within the balloon 23 to permit the physician to ascertain the location of the balloon when it is in the patient's vascular system.

The balloon 23, which is adjacent the distal end of the catheter body 21, has an inflatable portion 65, attachment portions 67 and 69 on opposite sides of the inflatable portion 65 which are sealed to the catheter body 21 and the tube 57, respectively, and the tubular distal portion 59. The balloon 23, which is constructed of a suitable plastic, such as polyethylene, may have the attachment portions 67 and 69 shrunk onto the catheter body 21 and the tube 57. By tightly shrinking the attachment portion 67 onto the catheter body 21, the catheter body may be compressed somewhat radially inwardly to form an inwardly extending annular shoulder 71 which tends to make the periphery of the attachment portion 67 approximately coextensive with the periphery of the catheter body 21. This minimizes changes in cross section along the length of the catheter 13.

The tube 57 extends completely through the inflatable portion 65, which is of larger cross-sectional area than the tube and the catheter body 21. However, the tube 57 does not project completely through the balloon 23 in that the tubular distal portion 59 extends distally of the tube 57 to form the distal end 73 of the catheter 13. The tubular distal portion 59 is of smaller cross section than the tube 57 and is smoothly and gradually blended into such smaller cross section by an inclined annular wall section 75 which extends distally from the distal end of the tube 57. The tubular distal portion 59 terminates distally in a cylindrical section 77 which defines a distal port 79 at the distal end 73.

The balloon 23 is integrally constructed, and the tubular distal portion 59 is resiliently flexible. Preferably, the tubular distal portion 59 is more flexible than regions of the catheter body 21 adjacent the tube 57.

First means is provided for introducing a purging liquid to the lumen 35. Although this means can take different forms, in the embodiment illustrated, it includes the purge fitting 15 and a vent tube 81 carried by the purge fitting. As shown in FIG. 2, the purge fitting 15 is removably coupled to the connector 29 in a conventional manner. The purge fitting 15 is in the form of a Y-fitting having a first leg 83 in communication with the lumen 35 through a common passage 85 and a passage 51 of the connector 29. The inner tube 45, which defines the proximal extension of the lumen 37, extends completely through the passage 51 of the connector 29 and into the passage 85 of a second leg 87 of the purge fitting 15. The vent tube 81 is slidably received within the passage of the second leg 87, and the vent tube slidably receives the proximal end of the inner tube 45 as shown in FIG. 2. The vent tube 81 terminates in a vent opening 88.

With the purge fitting 15 coupled to the connector 29, the catheter assembly 11 can be used to purge air from the balloon 23 as shown in FIG. 7. The first leg 83 is coupled to a source of the purging liquid (not shown), and the distal end of the balloon is pointed downwardly. The purging liquid is then passed in series through the first leg 83, the passages 85 and 51, the lumen 35, the inflatable portion 65 of the balloon 23, the lumen 37 and the vent tube 81. The passing of the purging liquid in series through the lumens 35 and 37 forces the air in the balloon out through the lumen 37 and the vent tube 81 to the atmosphere. The purging liquid is passed in series through the lumens 35 and 37 in this fashion at least until the purging liquid emerges from the vent opening 88. At this time, it is known that all of the air has been purged from the balloon 23.

Means is also provided for introducing an inflation liquid to the balloon 23 and for discharging the inflation liquid from the balloon. Although this means can take different forms, in the embodiment illustrated, it includes a syringe 89 (FIG. 8) for accomplishing both of these purposes. More specifically, the purge fitting 15 is removed from the connector 29, and the syringe 89 is attached to the proximal end of the connector. The vent tube 81 can be easily removed with the purge fitting 15 by pulling it off the proximal end of the inner tube 45. The syringe 89 includes the usual barrel 91 and plunger 93 which is movable to the right (as viewed in FIG. 8) on a discharge stroke and to the left (as viewed in FIG. 8) in a suction stroke.

With the syringe 89 charged with inflation liquid, the plunger 93 on the discharge stroke introduces an inflation liquid in parallel through both of the lumens 35 and 37 to inflate the balloon as shown in dashed lines in FIG. 8. More specifically, the inflation liquid from the barrel 91 is forced through the passage 51 to the lumen 35 and forced directly from the barrel into the inner tube 45. Similarly, by moving the plunger 93 on the suction stroke, the inflation liquid is discharged from the balloon 23 in parallel through both of the lumens 35 and 37 to deflate the balloon and move the inflation liquid back into the barrel 91. Because both of the lumens 35 and 37 are used in parallel to inflate and deflate the balloon 23, inflation and deflation of the balloon takes place very rapidly.

In use of the catheter assembly 11, air is first purged from the balloon 23 as described above. Next, the catheter is inserted into the vascular system of the patient using known techniques to place the balloon 23 in the region of the vascular system, such as an appropriate artery, which is to be dilated. After the purge fitting 15 has been replaced with the syringe 89, the balloon 23 is inflated as described above to dilate the desired region of the vascular system and then deflated to discontinue dilation. Inflation and deflation of the balloon 23 are carried out rapidly. The dilation procedure may be carried out repeatedly within the artery before the catheter is removed from the patient's vascular system. The purging liquid and the inflation liquid may be the same liquid and may be any of a variety of known solutions, such as a mixture of Renographen and saline.

During the insertion of the catheter 13, the tubular distal portion 59, being of small diameter, passes through the artery wth relative ease. The inclined wall section 75 provides essentially no shoulder that could cause damage to the tissue. In addition, the flexible nature of the tubular distal portion 59 further minimizes likelihood of injury to the tissue.

Although an exemplary embodiment of the invention has been shown and described, many changes, modifications and substitutions may be made by one having ordinary skill in the art without necessarily departing from the spirit and scope of this invention.

We claim:

1. A method of dilating a region of a patient's vascular system comprising:
   providing a catheter having a distal end, at least first and second lumens, and a balloon adjacent the distal end with the first and second lumens extending to the interior of the balloon;
   passing as purging liquid in series through the first lumen, the balloon and the second lumen to purge air from the balloon out through the second lumen;
   inserting the catheter into the patient's vascular system to place the balloon in the region of the patient's vascular system which is to be dilated;
   thereafter passing an inflation liquid in parallel through the first and second lumens to the balloon to inflate the balloon to dilate such region of the vascular system; and
   discharging the inflation liquid from the balloon in parallel through the first and second lumens to deflate the balloon.

2. A method as defined in claim 1 wherein said first-mentioned step of passing is carried out with the distal end of the balloon pointed downwardly.

3. A method as defined in claim 1 wherein said step providing includes providing a vent opening for the second lumen adjacent the proximal end of the second lumen and said first-mentioned step of passing is carried out at least until the purging liquid emerges from the vent opening.

4. A method as defined in claim 1 wherein said region of the vascular system is an artery.

5. A catheter assembly adapted to dilate as tubular body member comprising:
   a catheter having a distal end, a proximal end, means for defining at least first and second lumens, a balloon adjacent the distal end with the first and second lumens communicating with the interior of the balloon and a connector adjacent said proximal end;
   first means removably mountable on the connector for introducing a purging liquid to the first lumen whereby the purging liquid can flow in series through the first lumen, the balloon and the second lumen to purge air from the balloon out through the second lumen; and
   second means removably mountable on the connector for introducing an inflation liquid through the first and second lumens to the balloon to inflate the balloon and for discharging the inflation liquid from the balloon through the first and second lumens to deflate the balloon.

6. A catheter assembly as defined in claim 5 wherein said second lumen extends through the connector and said first means includes a purge fitting having a first leg communicable with said first lumen at said connector and a second leg for receiving said second lumen, and said first leg is communicable with a source of the purging liquid.

7. A catheter assembly as defined in claim 5 wherein said second means includes a syringe mountable on the connector, said syringe has pumping and suction strokes, said syringe introducing the inflation liquid to the first and second lumens on the pumping stroke and withdrawing the inflation liquid from the balloon through the first and second lumens on the suction stroke.

8. A catheter assembly as defined in claim 5 wherein the catheter includes a catheter body, said first and second lumens and a third lumen extend through the catheter body, an extension tube coupled to the catheter body in communication with the third lumen and having a passage therethrough which forms an extension of the third lumen, said extension tube extends partially through the balloon, said balloon having an inflatable portion communicating with the first and second lumens, attachment portions on opposite sides of the inflatable portion sealed to the catheter body and the tube, respectively, and a tubular distal portion extending distally beyond the tube to form an extension of the third lumen and to define the distal end of the catheter.

9. A catheter assembly as defined in claim 8 wherein the tubular distal portion is of smaller cross section than the tube and is smoothly blended into such smaller cross section.

10. A catheter assembly as defined in claim 9 wherein the tubular distal portion is more flexible than the regions of the catheter body adjacent the tube.

11. A catheter as defined in claim 6 including a vent tube carried by the first means and slidably receiving a proximal end of the second lumen when the first means is mounted on the connector whereby the purging liquid can be vented through the vent tube and the vent tube can be removed from the second lumen.

12. A catheter as defined in claim 5 wherein said lumens terminate at an end of the balloon.

13. A catheter comprising:

an elongated catheter body adapted for insertion into the vascular system of a patient and having proximal and distal ends, a balloon inflation lumen and a through lumen;

a flexible extension tube coupled to the catheter body in communication with the through lumen and extending distally of the catheter body, said extension tube having a passage therethrough which forms an extension of the through lumen;

an inflatable balloon adjacent the distal end of the catheter body; and said balloon having an inflatable portion in communication with the balloon inflation lumen, attachment portions on opposite sides of the inflatable portion sealed to the catheter body and the tube, respectively, and an at least somewhat flexible tubular distal portion extending distally beyond the tube to form an extension of the through lumen and to define a distal end of the catheter.

14. A catheter as defined in claim 13 wherein said tubular distal portion is more flexible than regions of the catheter body adjacent the tube.

15. A catheter as defined in claim 13 wherein the tubular distal portion is of smaller cross section than the tube and smoothly blended into such small cross section without an abrupt change of cross section.

16. A catheter as defined in claim 15 wherein said tube is partly received within the distal portion of the through lumen in the catheter body.

* * * * *